(12) United States Patent
Nagamizu

(10) Patent No.: US 8,172,409 B2
(45) Date of Patent: May 8, 2012

(54) IMAGE PICKUP APPARATUS AND ENDOSCOPE

(75) Inventor: Hiroyuki Nagamizu, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 52 days.

(21) Appl. No.: 12/797,046

(22) Filed: Jun. 9, 2010

(65) Prior Publication Data

US 2010/0309553 A1    Dec. 9, 2010

Related U.S. Application Data

(63) Continuation of application No. PCT/JP2009/068120, filed on Oct. 21, 2009.

(30) Foreign Application Priority Data

Nov. 11, 2008    (JP) .................... 2008-289071

(51) Int. Cl.
*G02B 7/18* (2006.01)
*A61B 1/06* (2006.01)

(52) U.S. Cl. .................... 359/512; 600/169
(58) Field of Classification Search .......... 359/512; 385/117, 118; 600/101, 169
See application file for complete search history.

(56) References Cited

U.S. PATENT DOCUMENTS

2008/0228035 A1 * 9/2008 Hagihara et al. .......... 600/121

FOREIGN PATENT DOCUMENTS

| EP | 1 955 645 A1 | 8/2008 |
|---|---|---|
| JP | 51-114041 | 9/1976 |
| JP | 55-68349 | 5/1980 |
| JP | 01-185517 | 7/1989 |
| JP | 02-257926 | 10/1990 |
| JP | 3-33815 | 2/1991 |
| JP | 9-43723 | 2/1997 |
| JP | 11-47080 | 2/1999 |
| JP | 2000-241699 | 9/2000 |
| JP | 2000-298229 | 10/2000 |
| JP | 2006-000282 | 1/2006 |
| JP | 2007-162567 | 6/2007 |

OTHER PUBLICATIONS

Extended European Search Report dated Aug. 23, 2011 in counterpart European Patent Application No. EP 09 82 6003.7.
International Search Report dated Nov. 24, 2009.

* cited by examiner

*Primary Examiner* — Alessandro Amari
(74) *Attorney, Agent, or Firm* — Scully, Scott, Murphy & Presser, P.C.

(57) ABSTRACT

An image pickup apparatus has a heater device including a heater and a temperature sensor. The heater device is arranged outside the effective light beam range of an objective optical system, with a predetermined air gap between the heater device and an inner circumferential surface of a rigid member that holds a cover glass. The heater device is pressed to the cover glass by an elastic member disposed at an outer circumferential portion of a protruding frame that holds a lens at a distal end. An electrical connection portion of the heater and an electrical connection portion of the temperature sensor of the image pickup apparatus are disposed facing each other with respect to an optical axis, on a proximal end side that is further to the rear than a distal end face of a lens on a distal end side of a front group lens unit that is a side on which a height of an effective light beam of the objective optical system is relatively low.

13 Claims, 5 Drawing Sheets

IMAGE PICKUP APPARATUS AND ENDOSCOPE

CROSS REFERENCE TO RELATED APPLICATION

This application is a continuation application of PCT/JP2009/068120 filed on Oct. 21, 2009 and claims benefit of Japanese Application No. 2008-289071 filed in Japan on Nov. 11, 2008, the entire contents of which are incorporated herein by this reference.

BACKGROUND OF THE INVENTION

1. Field of the Invention

The present invention relates to an image pickup apparatus that includes an anti-fogging portion that prevents fogging of a surface of an optical member disposed at a distal end position of an objective optical system, and an endoscope that is equipped with the image pickup apparatus.

2. Description of the Related Art

An image pickup apparatus that has an image pickup device that performs photoelectric conversion of an optical image of an object is applied to an endoscope used for observation/treatment or the like of inside of a body cavity or for inspection/repair or the like of inside of plant facilities for industrial use. However, when a distal end portion of an endoscope is inserted into a high temperature and high humidity environment, fogging may occur on a cover glass that is an optical member disposed at the distal end portion.

Therefore, Japanese Patent Application Laid-Open Publication No. 2006-282 discloses a defogging apparatus of an endoscope in which the surface of an optical member at a distal end position of an observation optical system is subjected to hydrophilic treatment and which is equipped with a heating portion that heats the optical member to perform a defogging action.

Further, Japanese Patent Application Laid-Open Publication No. 2007-162567 discloses disposing a heat generating portion that heats a cover glass and a temperature detection portion that detects a temperature of a cover glass at positions that are not included in the range of the field of view for image pickup in order to prevent a defogging apparatus from affecting the image-pickup field of view of an image pickup portion.

SUMMARY OF THE INVENTION

An image pickup apparatus of an embodiment of the present invention includes: an objective optical system that has a first optical member disposed at a distal end position and a second optical member disposed on a proximal end side of the first optical member; an anti-fogging portion that prevents fogging of a surface of the first optical member; and an image pickup device; wherein the anti-fogging portion has a heating member that heats the first optical member and a temperature measuring member that measures a temperature of the first optical member, in which the heating member is disposed on an outer circumference side of the second optical member and contacts against an inner surface on a proximal end side of the first optical member, and a proximal end side thereof is disposed further on a proximal end side than a surface on a distal end side of the second optical member.

An endoscope of another embodiment of the present invention is an endoscope in which an image pickup apparatus is arranged at a distal end portion of an insertion portion, the image pickup apparatus including: an objective optical system having a first optical member disposed at a distal end position and a second optical member disposed on a proximal end side of the first optical member, an anti-fogging portion that prevents fogging of a surface of the first optical member, and an image pickup device; wherein the anti-fogging portion has a heating member that heats the first optical member and a temperature measuring member that measures a temperature of the first optical member, in which the heating member is disposed on an outer circumference side of the second optical member and contacts against an inner surface on a proximal end side of the first optical member, and a proximal end side thereof is disposed further on a proximal end side than a surface on a distal end side of the second optical member.

DETAILED DESCRIPTION OF THE PREFERRED EMBODIMENT

Figure 1:
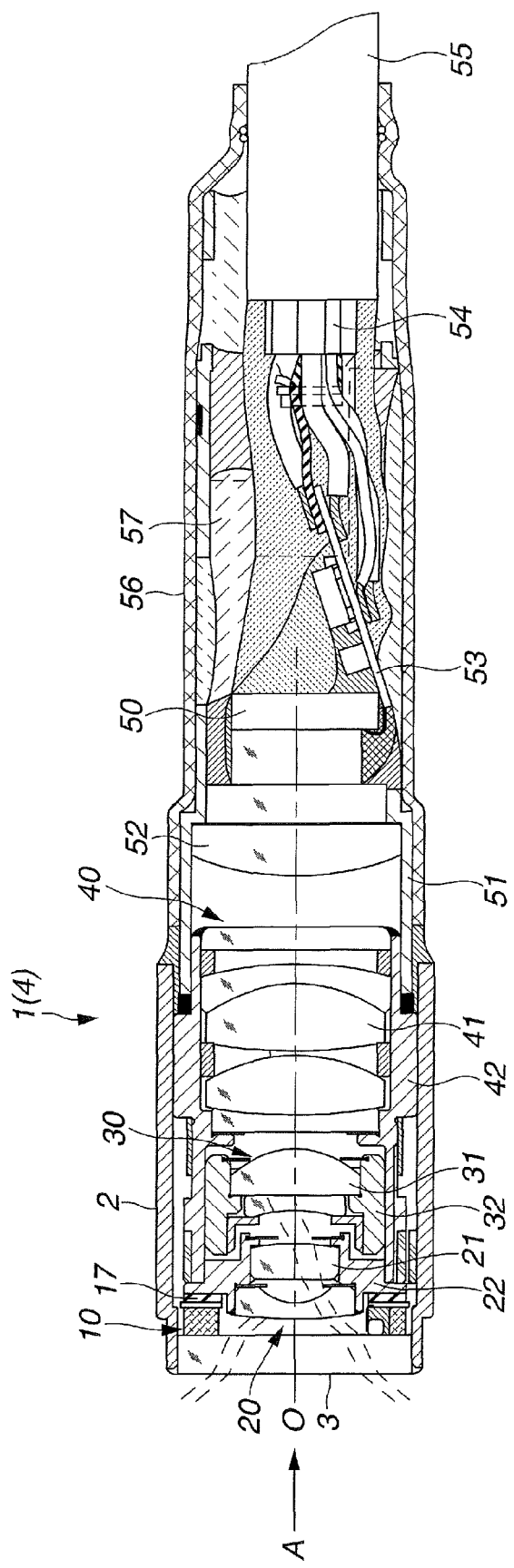
FIG. 1 is a configuration diagram that illustrates an image pickup apparatus provided at a distal end portion of an insertion portion of an endoscope.

An embodiment of the present invention is described hereunder referring to the drawings.

An image pickup apparatus of the present invention has an anti-fogging portion that has a function that stops fogging of an optical member at a distal end of an objective optical system that forms an optical image of an object on an image pickup surface of an image pickup device. The image pickup apparatus of the present invention, for example, is applied to an endoscope or the like and is provided at a distal end portion of an elongated insertion portion that is inserted into a body cavity. An endoscope equipped with the image pickup apparatus of the present invention is not limited with respect to whether the insertion portion thereof has flexibility, whether the endoscope includes a bending portion, or with respect to whether the field of use of the endoscope is medical use, industrial use, or the like.

According to the present embodiment, an image pickup apparatus that is used in an endoscope 4 that includes an objective optical system in which a lens inside the image pickup apparatus can be moved backward and forward to execute a focus function or a zooming/tele function is described as an example. Although not illustrated in the drawing, an image pickup apparatus 1 shown in FIG. 1 is arranged in a metal frame at a distal end portion of an insertion portion of the endoscope 4. A bendable bending portion and a flexible tube are provided on a proximal end side of the distal end portion on the image pickup apparatus 1. Further, an operation portion that connects with a grasping portion is provided on the proximal end side, and the endoscope 4, more specifically, the image pickup apparatus 1, is connected with a signal processing apparatus of a body section via a universal cable that extends from the operation portion. Hereunder, the proximal end side is also referred to as the "rear" and the distal end side is also referred to as the "front".

The objective optical system of the image pickup apparatus 1 has a cover glass 3 as a first optical member, and a second optical member including a plurality of optical members that is disposed on a proximal end side of the cover glass 3. The distal end portion of the image pickup apparatus 1 has a substantially cylindrical rigid member 2. The cover glass 3 that has a disk shape that forms the distal end face of the objective optical system is fitted to the distal end of the rigid member 2. A heater unit 10 as an anti-fogging portion that heats the cover glass 3 to perform defogging is arranged on the proximal end side of the cover glass 3 so as to be outside the range of field of view for image pickup. The second optical member includes three optical members that each has a plurality of lenses. The three optical members are a front group lens unit 20 on the distal end side, a moving lens unit 30, and a rear group lens unit 40 on the proximal end side. The moving lens unit 30 includes a plurality of moving lenses that can move back and forth in the optical axis O direction of the objective optical system. The outer diameter of the cover glass 3 is larger than the outer diameter of a lens 21a that constitutes the distal end face of the front group lens unit 20, and the heater unit 10, described later, is arranged by also using a space on the outer circumference of the lens 21a.

The front group lens unit 20 includes a front group lens frame 22 as a holding frame that holds and fixes a plurality of front group lenses 21. The front group lens frame 22 is fitted to a distal end side of a rear group lens frame 42 that holds and fixes a plurality of rear group lenses 41. Inside the rear group lens frame 42, a moving lens frame 32 that holds and fixes a plurality of moving lenses 31 is disposed so as to be slidable (movable back and forth) along the optical axis O direction between the front group lens unit 20 and the rear group lens unit 40.

A front end portion of an image pickup device holding frame 51 that holds an image pickup device 50 constituted by a solid-state image pickup device such as a CCD or a CMOS is insertedly fitted to a rear end portion of the rear group lens frame 42 so as to be fixed thereto. A plurality of lenses 52 that face the rear group lens unit 40 having the same optical axis O, and the image pickup device 50 having an image pickup surface on a rear end face side of the plurality of lenses 52 are held and fixed inside the image pickup device holding frame 51. The image pickup device 50 is a substantially rectangular shape in which the lateral size of the image pickup surface is larger than the vertical size. The image pickup surface is disposed so that the long-side direction thereof is in the vertical direction in FIG. 1. Consequently, the height of an effective light beam of the objective optical system of the image pickup apparatus 1 is not constant, and the height of the effective light beam is low (small) in the vertical direction in FIG. 1 that corresponds to the longitudinal (short-side) direction of the image pickup device 50, and the height thereof is high (large) in a perpendicular direction on the surface of the sheet of FIG. 1 that corresponds to the lateral (long-side) direction of the image pickup device 50.

A multilayer substrate 53 on which is mounted a circuit chip for driving and processing input and output signals is arranged on the rear side of the image pickup surface of the image pickup device 50. The multilayer substrate 53 and the image pickup device 50 are electrically connected via an unshown flexible printed circuit (FPC). The multilayer substrate 53 is connected to a plurality of signal wires of a cable 54 that is insertedly disposed in a cable holding member 55, and is connected to an unshown signal processing apparatus via a cable that extends from the endoscope.

A covering member 56 that is a heat-shrinkable tube covers an outer circumferential surface other than the distal end portion that fits to the rigid member 2 of the image pickup device holding frame 51. The area from the image pickup device holding frame 51 to the distal end portion of the cable holding member 55 is integrally covered by the covering member 56. A filling agent 57 made of a resin material or the like is filled inside the covering member 56, and fixes and protects the image pickup device 50 and the multilayer substrate 53.

The filling agent 57 is not limited to one kind of agent, and a plurality of kinds of filling agents may be used as the filling agent 57 in accordance with the filling location. For example, a filling agent with a high insulation property is used on a proximal end side (rear side) at the rear of the image pickup device 50, and a filling agent with good thermal conductivity is used between the side surface of the image pickup device 50 and the image pickup device holding frame 51. Thus, heat that is generated when driving the image pickup device 50 can be efficiently conducted to the cover glass 3 at the front via the image pickup device holding frame 51 and the rigid member 2. More specifically, heat generated by the image pickup device 50 can be utilized to defog the cover glass 3.

Figure 2:
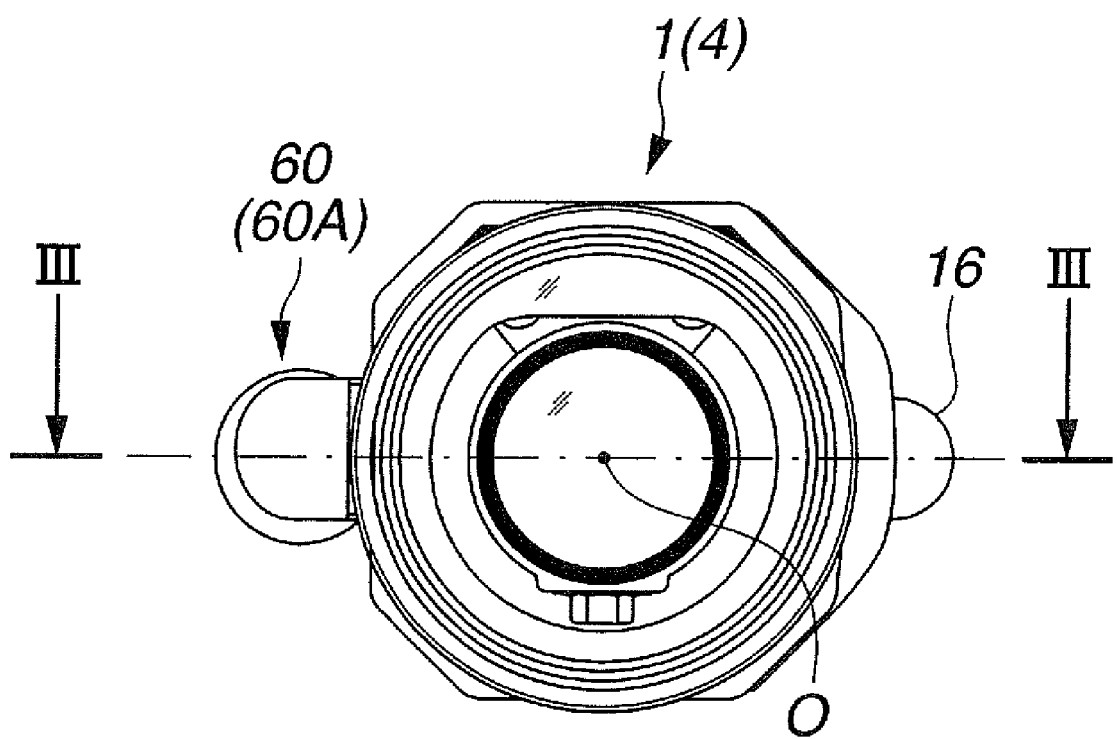
FIG. 2 is a front view as seen from the direction of an arrow A in FIG. 1 of the image pickup apparatus provided at the distal end portion of the insertion portion of the endoscope.

The lens moving mechanism 60 will now be described using FIG. 2 and FIG. 3. As shown in FIG. 2, the lens moving mechanism 60 that moves the moving lens unit 30 back and forth in the optical axis O direction is arranged on a side that corresponds to the long side of the image pickup surface of the image pickup device 50 of the image pickup apparatus 1. More specifically, the image pickup apparatus 1 includes the lens moving mechanism 60 that is an optical member moving portion that moves the moving lens unit 30 in the optical axis direction O of the objective optical system. The moving lens unit 30 is one optical member of the objective optical system.

Figure 3:
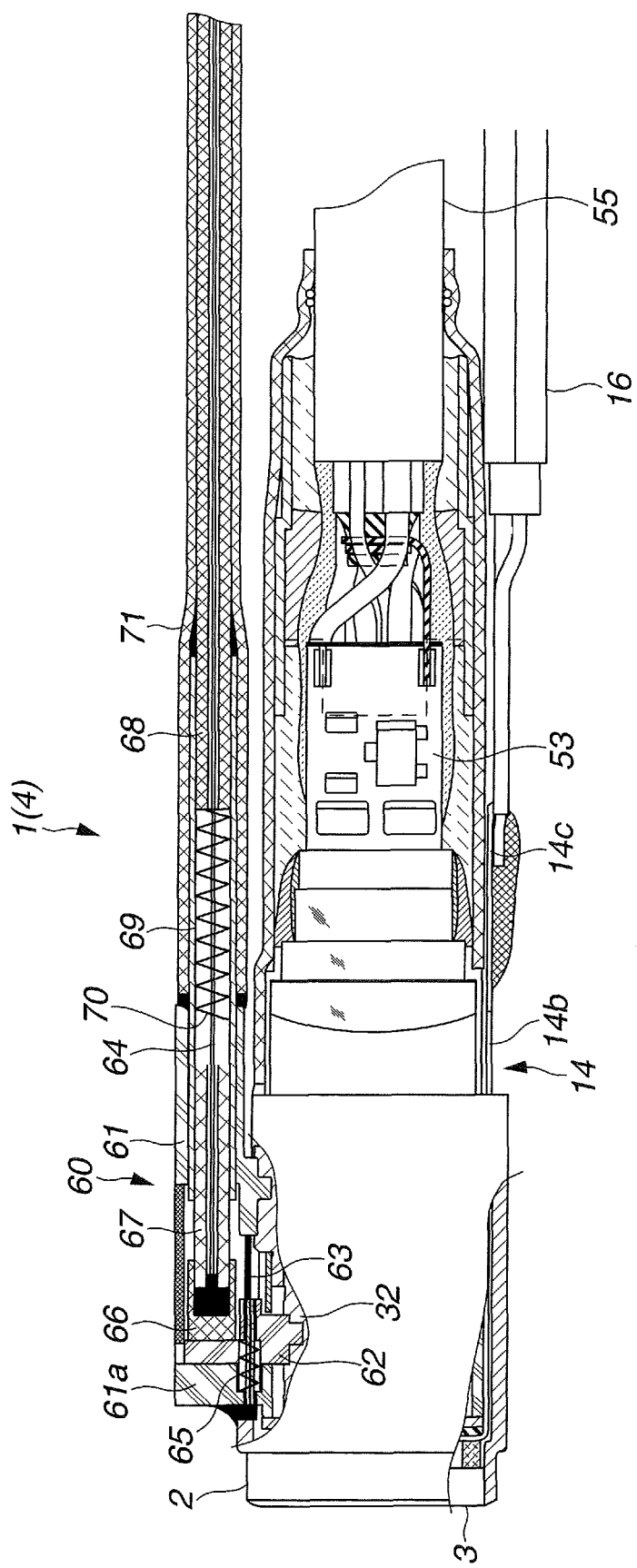
FIG. 3 is an explanatory drawing that illustrates the configuration of a lens moving mechanism by means of a cross section along a line in FIG. 2 of the image pickup apparatus provided at the distal end portion of the insertion portion of the endoscope.

As shown in FIG. 3, the lens moving mechanism 60 includes an actuator holding frame 61 that is arranged so as to cover an opening portion provided in the outer circumference of the rigid member 2 of the image pickup apparatus 1, a connecting rod 62 that is provided inside the actuator holding frame 61 and that is engaged with an outer circumferential part of the moving lens frame 32, a guide shaft 63 that enables precise movement of the connecting rod 62 in a direction parallel to the optical axis O inside a notch provided in the outer circumferential part of the rear group lens frame 42, and a drive wire 64 for moving the connecting rod 62 back and forth along the guide shaft 63.

The actuator holding frame 61 includes a contact portion 61a that regulates movement to the distal end side of the connecting rod 62. A spring 65 that urges the connecting rod 62 in a direction away from the contact portion 61a is interposed between the contact portion 61a and the connecting rod 62.

The drive wire 64 is a wire with a diameter of approximately several tens of microns that is formed with a shape memory alloy (SMA) that shrinks when heated and expands when cooled. Hereunder, the drive wire 64 is referred to as "SMA wire 64". The SMA wire 64 is fixedly mounted so as to fold back inside a base 66 that is fixedly installed in the connecting rod 62, and extends from an insulating pipe 67 fitted to the base 66 to the operation portion side by passing through the inside of a spring-stopping pipe 68.

A portion of the insulating pipe 67 and the spring-stopping pipe 68 is fitted inside the guide pipe 69 that is mated to the actuator holding frame 61. Inside the guide pipe 69, an end of a spring 70 that is sheathed over the SMA wire 64 and that urges the connecting rod 62 forward contacts against the spring-stopping pipe 68. An insulating tube 71 is covered over the guide pipe 69, and the outer circumference of the spring-stopping pipe 68 that is exposed from the guide pipe 69 and extends therefrom is covered by the insulating tube 71.

An end on the operation portion side of the SMA wire 64 is fixed by a block body or the like that is connected to an electric cable (first cable) 60A that is a wiring system that extends from the lens moving mechanism 60. The connecting rod 62 moves back and forth based on the relation between a shrinking action produced by electrification and heat generation of the SMA wire 64 and the urging forces of the springs 65 and 70. As a result, since the moving lens unit 30 that is engaged with the connecting rod 62 moves back and forth in the optical axis O direction, the image pickup apparatus 1 can perform a focusing operation or a zooming/tele operation.

More specifically, when performing a focusing operation or a zooming/tele operation, a current is passed to the SMA wire 64 through a cable 60A by an unshown control apparatus so that the SMA wire 64 generates heat to cause the length thereof to shrink. Thereupon, the connecting rod 62 connected to the SMA wire 64 is pulled in opposition to the urging forces of the springs 65 and 70, so that the moving lens unit 30 moves to the rear group lens unit 40 side while being guided by the guide shaft 63. When passage of a current to the SMA wire 64 stops, the SMA wire 64 naturally cools and returns to its original length and the connecting rod 62 is pushed forward by the urging forces of the springs 65 and 70. As a result, the moving lens unit 30 moves forward. At this time, forward movement of the moving lens unit 30 is restricted by the front face of the connecting rod 62 contacting against a contact portion 61a.

As described above, while maintaining a simple configuration, the image pickup apparatus 1 that has the lens moving mechanism 60 that uses the SMA wire 64 is capable of a focusing operation or a zooming/tele operation.

Figure 4:
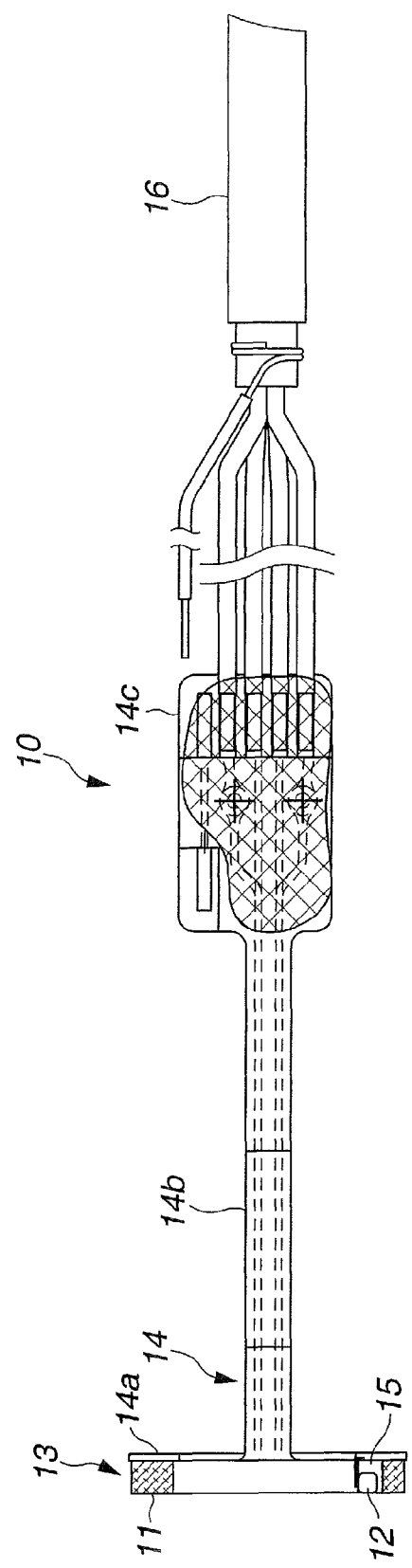
FIG. 4 is a configuration diagram of a heater unit.
Figure 5:
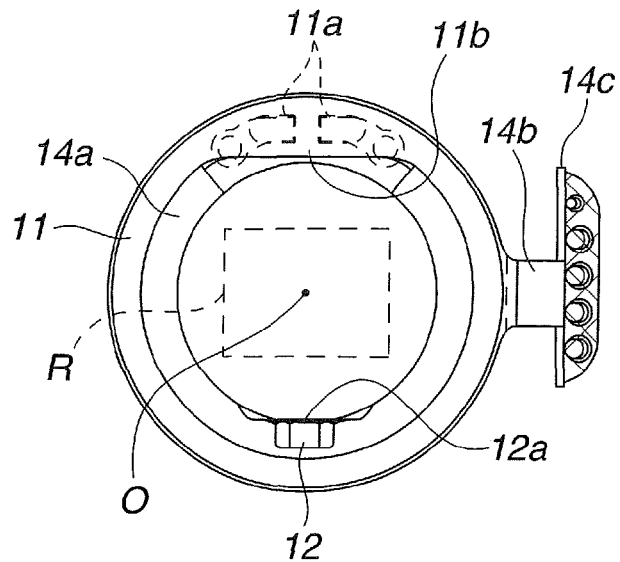
FIG. 5 is a front view of a heater unit as seen from the direction of an arrow C in FIG. 4.
Figure 6:
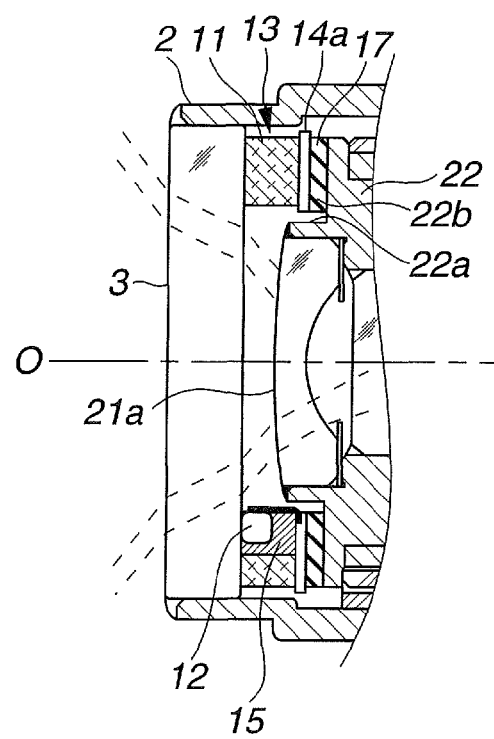
FIG. 6 is an enlarged view of the distal end of the image pickup apparatus.

Next, the heater unit 10 that is an anti-fogging portion arranged between the cover glass 3 at the distal end of the image pickup apparatus 1 and the front group lens unit 20 is described using FIG. 4, FIG. 5, and FIG. 6.

The heater unit 10 includes as principal components a heater device 13 that integrally includes a heater 11 as a heating member that heats the cover glass 3 and a temperature sensor 12 as a temperature measuring member that measures the temperature of the cover glass 3, and a printed circuit 14 constituted by an FPC or the like for connecting the heater 11 and the temperature sensor 12 to a control apparatus (unshown).

The heater 11 that constitutes a principal portion of the heater device 13 is a heating element in which, for example, a resistance wire pattern or a nichrome wire or the like is integrated into a ceramic substrate or a ceramic heater such as a PTC heater, and which is formed in a substantially ring shape that has an opening region at the center. The outer diameter of the substantially ring-shaped heater 11 is smaller than the outer diameter of the cover glass 3. Further, the thickness of the heater 11 is greater than or equal to a distance from the inner surface (surface on proximal end side) of the cover glass 3 to the distal end face of the front group lens unit 20. Furthermore, the substantially ring-shaped heater 11 is formed to a size that does not obstruct an effective light beam R that is incident on an image pickup region of the image pickup device 50 when the inner diameter side of the substantially ring-shaped heater 11 is disposed so as to contact against the inner surface of the cover glass 3.

In this connection, a surface on the distal end side of the heater 11 may be subjected to blast processing to prevent flares caused by heating of the cover glass 3. Further, a flare diaphragm with an inner diameter that does not obstruct the effective light beam R may be provided between the heater 11 and the cover glass 3. When using a flare diaphragm, heat can be conducted with good efficiency from the heater 11 to the cover glass 3 by making the thermal conductivity of the material forming the flare diaphragm less than the thermal conductivity of the cover glass 3.

The temperature sensor 12 is constituted using, for example, a resistance temperature sensor such as a thermistor. The temperature sensor 12 is fixed via a heat insulating material 15 to a wall portion on an inner circumference side of the heater 11 that is formed in a substantially ring shape. More specifically, heat from the heater 11 is not directly transferred to the temperature sensor 12. Further, the temperature sensor 12 is disposed so that the surface of the heater 11 that contacts against the cover glass 3 and a temperature measuring surface of the temperature sensor 12 are on the same plane. More specifically, the temperature sensor 12 is arranged so that the temperature of the cover glass 3 can be accurately detected.

The printed circuit 14 is formed with, for example, polyimide (PI) or liquid crystal polymer (LCP) or the like. The printed circuit 14 includes a substantially ring-shaped electrode substrate portion 14a that is attached to a proximal end face (face on opposite side to face that contacts against the cover glass 3) of the heater 11, an elongated conductor wire portion 14b that is folded at an approximately right angle and extends from the electrode substrate portion 14a, and a cable connection portion 14c with a wide width that is provided at an end of the conductor wire portion 14b. A plurality of core wires of a cable (second cable) 16 that is a wiring system for connecting to the control apparatus are connected by soldering or the like to the cable connection portion 14c.

The printed circuit 14 that is formed with PI or LCP has excellent mechanical toughness and heat resistance, and has a low coefficient of water absorption. It is thus possible to prevent the entry of steam to the inner surface of the cover glass 3 due to water absorption when subjecting the endoscope to autoclave sterilization or the like. There is also the advantage that durability with respect to repeated bending can be improved. These advantages can be further improved by using gold plating instead of nickel plating as the plating for a conductor wire on the substrate.

As shown in FIG. 5, an electrode terminal 11a (electrical connection portion for heating) of the heater 11 and an electrode terminal 12a (electrical connection portion for measurement) of the temperature sensor 12 that are connected to the electrode substrate portion 14a are disposed at positions facing each other that sandwich the optical axis O therebetween, and are provided at positions corresponding to the long side of the image pickup device 50, more specifically, on a side on which an effective light beam of the objective optical system is low. Since the effective light beam is not obstructed even if a space at a position corresponding to the long side of the image pickup device 50 is made narrow, the electrode terminal 11a of the heater 11 is provided at a wide-width portion 11b that spreads from the circumference side towards the center side. The electrode terminal 12a of the temperature sensor 12 extends towards the electrode substrate portion 14a from a side face on the inner diameter side facing the electrode terminal 11a of the heater 11, and is connected to the electrode substrate portion 14a. The electrode substrate portion 14a is formed, for example, with an outer diameter that is approximately the same as the outer diameter of the heater 11 and with an inner diameter that is somewhat smaller than the inner diameter of the heater 11.

As described above, all of the constituent elements of the heater unit 10 are disposed at positions that are on the outside of the effective light beam range of the objective optical system.

Further, in the heater unit 10, inside the distal end portion of the image pickup apparatus 1, the electrode terminal 11a of the heater 11 and the electrode terminal 12a of the temperature sensor 12 are disposed at positions corresponding to the long side of the image pickup device 50. Consequently, a second cable 16 that is connected to the conductor wire portion 14b and the cable connection portion 14c of the printed circuit 14 is disposed on the opposite side to the first cable 60A of the lens moving mechanism 60. In other words, as shown in FIG. 2, the first cable 60A and the second cable 16 are disposed at positions facing each other with respect to the optical axis O.

Further, as shown in FIG. 1 and FIG. 6, the heater device 13 that includes the heater 11 and the temperature sensor 12 is arranged so that there is a predetermined air gap between the outer circumferential face thereof and the inner circumferential face of the rigid member 2 that holds the cover glass 3, and is held via an elastic member 17 that has a heat insulating property between the cover glass 3 and the front group lens frame 22. More specifically, in the front group lens frame 22, a portion that holds the lens 21a that constitutes the distal end face among the plurality of lenses 21 included in the front group lens unit 20 is integrally formed as a protruding frame 22a that protrudes to the front, and an elastic member 17 is arranged at a flat portion 22b formed in the outer circumferential part of the protruding frame 22a and presses the heater device 13 to the cover glass 3.

As described above, the heater 11 has an opening region that does not obstruct an effective light beam that is incident on an image pickup region of the image pickup device 50, and has a thickness that is greater than or equal to a distance from the cover glass 3 to the distal end face of the lens 21a. Therefore, the protruding frame 22a of the front group lens frame 22 is housed inside the opening of the heater device 13, and the heater device 13 is disposed at a position that is outside of the effective light beam range (area indicated by a dashed line in FIG. 1, FIG. 5, and FIG. 6) of the objective optical system. Further, a connection portion to the electrode substrate portion 14a of the heater 11 and a connection portion to the electrode substrate portion 14a of the temperature sensor 12 are disposed facing each other with respect to the optical axis O at positions on a proximal end side that is further to the rear than the distal end face of the lens 21a on the distal end side of the front group lens unit 20 that is a side on which the height of the effective light beam of the objective optical system is relatively low.

When using the endoscope 4 having an image pickup system configured as described above to, for example, insert the image pickup apparatus 1 inside a body cavity to conduct observation, first, a current is passed to the heater 11 and the temperature of the cover glass 3 is controlled to an appropriate setting temperature based on a signal from the temperature sensor 12 before inserting the image pickup apparatus 1. The appropriate setting temperature is, for example, an appropriate setting temperature at which the upper-limit temperature of the cover glass 3 is not greater than 43° C., for example, a temperature such as 40° C. that does not cause low temperature burns to a living body.

Thus, the image pickup apparatus 1 is inserted into the abdominal cavity or the like of a patient in a state in which the heating temperature of the cover glass 3 produced by the heater 11 is held constant at an appropriate setting temperature such as, for example, 40° C. Normally, the inside of an abdominal cavity of a patient is, for example, an environment with a temperature of approximately 37° C. and a humidity of approximately 98% to 100%. However, when using the image pickup apparatus 1, it is difficult for water drops caused by moisture or the like generated from a living body to attach to the surface of the cover glass 3, and even if such water drops do attach to the surface of the cover glass 3 the water drops can be rapidly dried. Hence, the image pickup apparatus 1 can effectively prevent fogging.

At this time, the heater device 13 that includes the heater 11 and the temperature sensor 12 is disposed in close contact with the inner surface of the cover glass 3. More specifically, the heater device 13 is arranged with a predetermined air gap between the heater device 13 and the inner circumferential face of the rigid member 2 and is pressed to the cover glass 3 by the elastic member 17 that has a heat insulating property. The heater 11 and the temperature sensor 12 are thermally insulated via the heat insulating material 15. Consequently, according to the image pickup apparatus 1, it is possible to prevent heat of the heater 11 from being transferred to a site other than the cover glass 3 so that the cover glass 3 can be efficiently heated. The image pickup apparatus 1 can accurately measure the temperature of the cover glass 3 by means of the temperature sensor 12 and can perform precise temperature management.

Further, because an air gap is provided between the heater device 13 and the inner circumferential face of the rigid member 2, it is possible to obtain favorable heat insulating properties and favorable electrical insulation properties at the same time by means of the air gap. Thus, fogging of the cover glass 3 can be prevented while simultaneously preventing adverse effects produced by static electricity. In this connection, a configuration may be adopted in which a member that has excellent heat insulating properties and electrical insulation properties is arranged in the area between the heater device 13 and the inner circumferential face of the rigid member 2 instead of making that area an empty space.

A further feature of the image pickup apparatus 1 is that the heater device 13 thereof is disposed at a position that is outside the effective light beam range of the objective optical system, and thus the effective light beam of the objective optical system is not obstructed. Consequently, it is possible to obtain a favorable image-pickup field of view combined with an anti-fogging effect without obstructing the image-pickup field of view. Further, the electrode substrate portion 14a (electrical connection portion for heating) of the heater 11 and the electrode substrate portion 14a (electrical connection portion for measurement) of the temperature sensor 12 are disposed facing each other with respect to the optical axis O at positions on a proximal end side that is further to the rear than the distal end face of the lens 21a on the distal end side of the front group lens unit 20 that is a side on which the height of the effective light beam of the objective optical system is relatively low. Consequently, even if the heater device 13 is made with a small diameter, it is possible to secure an effective field of view while maintaining the strength of the electrical connection portion. As a result, it is possible to provide the image pickup apparatus 1 with a thin diameter and thereby contribute to improving the convenience and operability of the image pickup apparatus 1 as the endoscope 4.

In particular, the electrical connection portion for heating of the heater 11 and the electrical connection portion for measurement of the temperature sensor 12 are disposed facing each other at positions corresponding to the long side of the image pickup device 50. Hence, because a wide-width portion 11b is provided in the heater 11 by utilizing an opening region that is a wasted space that does not contribute to the effective field of view, and an electrical connection portion is provided in the wide-width portion 11b, the heater device 13 can be provided with a small diameter while securing a heat generation area and ensuring the strength of the electrical connection portion of the heater. In particular, in an apparatus that has the lens moving mechanism 60 for performing a focus function or a zooming/tele function, a significant advantage can be obtained by making the diameter of the image pickup apparatus thinner by providing the heater device 13 with a small diameter.

In this connection, naturally the endoscope 4 that includes the image pickup apparatus 1 has the same advantages as those of the image pickup apparatus 1.

The present invention is not limited to the above described embodiment and modification example, and various modifications and improvements can be made to the present invention within a range that does not depart from the spirit and scope of the present invention.

What is claimed is:

1. An image pickup apparatus comprising:
   an objective optical system including a first optical member disposed at a distal end position and a second optical member disposed on a proximal end side of the first optical member;
   an anti-fogging portion that prevents fogging of a surface of the first optical member; and
   an image pickup device;
   wherein:
   the anti-fogging portion includes a heating member that heats the first optical member, and a temperature measuring member that measures a temperature of the first optical member, in which the heating member is disposed on an outer circumference side of the second optical member and contacts against an inner surface on a proximal end side of the first optical member, and a proximal end side thereof is disposed further on a proximal end side than a surface on a distal end side of the second optical member,
   the heating member includes an electrical connection portion for heating and the temperature measuring member includes an electrical connection portion for measurement, and
   the electrical connection portion for heating and the electrical connection portion for measurement are disposed facing each other on a side on which the height of an effective light beam of the objective optical system is low.

2. The image pickup apparatus according to claim 1, further comprising:
   a holding frame that holds the second optical member,
   wherein:
   an outer diameter of the anti-fogging portion is smaller than an outer diameter of the first optical member, and
   the anti is disposed on an outer circumference side of the holding frame.

3. The image pickup apparatus according to claim 2, wherein the anti-fogging portion is disposed outside an effective light beam range of the objective optical system.

4. The image pickup apparatus according to claim 3, comprising an elastic member that is disposed on a proximal end side of the heating member,
   wherein the elastic member presses the heating member to the first optical member.

5. The image pickup apparatus according to claim 4, comprising an optical member moving portion that has a drive wire for moving one portion of optical members of the objective optical system in an optical axis direction of the objective optical system;
   wherein a first cable that is a wiring system that extends from the optical member moving portion and a second cable that is a wiring system that extends from the anti-fogging portion are disposed facing each other with respect to an optical axis of the objective optical system.

6. The image pickup apparatus according to claim 5, wherein the drive wire is formed with a shape memory alloy.

7. The image pickup apparatus according to claim 6, wherein the heating member is a ring-shaped heater that has a center portion through which a light beam that is incident on an image pickup region of the image pickup device can pass, and the heating member has a thickness that is greater than or equal to a distance between a surface on a proximal end side of the first optical member and a surface on a distal end side of the second optical member.

8. An endoscope comprising:
   an insertion portion; and
   an image pickup apparatus arranged at a distal end portion of the insertion portion, the image pickup apparatus comprising:
   an objective optical system including a first optical member disposed at a distal end position and a second optical member disposed on a proximal end side of the first optical member,
   an anti-fogging portion that prevents fogging of a surface of the first optical member, and
   an image pickup device;
   wherein:
   the anti-fogging portion includes a heating member that heats the first optical member and a temperature measuring member that measures a temperature of the first optical member, in which the heating member is disposed on an outer circumference side of the second optical member and contacts against an inner surface on a proximal end side of the first optical member, and a proximal end side thereof is disposed further on a proximal end side than a surface on a distal end side of the second optical member,
   the heating member includes an electrical connection portion for heating and the temperature measuring member includes an electrical connection portion for measurement, and
   the electrical connection portion for heating and the electrical connection portion for measurement are disposed facing each other on a side on which the height of an effective light beam of the objective optical system is low.

9. The endoscope according to claim 8, further comprising:
   a holding frame that holds the second optical member,
   wherein:
   an outer diameter of the anti-fogging portion is smaller than an outer diameter of the first optical member, and
   the anti-fogging portion is disposed on an outer circumference side of the holding frame.

10. The endoscope according to claim 9, wherein the anti-fogging portion is disposed outside an effective light beam range of the objective optical system.

11. The endoscope according to claim 10, comprising an elastic member that is disposed on a proximal end side of the heating member,
    wherein the elastic member presses the heating member to the first optical member.

12. The endoscope according to claim 11, comprising an optical member moving portion that has a drive wire for moving one portion of optical members of the objective optical system in an optical axis direction of the objective optical system;
  wherein a first cable that is a wiring system that extends from the optical member moving portion and a second cable that is a wiring system that extends from the anti-fogging portion are disposed facing each other with respect to an optical axis of the objective optical system.

13. The endoscope according to claim 12, wherein the drive wire is formed with a shape memory alloy.

* * * * *

UNITED STATES PATENT AND TRADEMARK OFFICE
CERTIFICATE OF CORRECTION

| | | |
|---|---|---|
| PATENT NO. | : 8,172,409 B2 | Page 1 of 1 |
| APPLICATION NO. | : 12/797046 | |
| DATED | : May 8, 2012 | |
| INVENTOR(S) | : Hiroyuki Nagamizu | |

It is certified that error appears in the above-identified patent and that said Letters Patent is hereby corrected as shown below:

It Should Read:

Column 9, line 56 (claim 2, line 7): the anti-fogging portion is disposed on an outer circumference side of the Signed and Sealed this
Eleventh Day of September, 2012

David J. Kappos
*Director of the United States Patent and Trademark Office*